United States Patent [19]
Heckrodt et al.

[11] 3,980,890
[45] Sept. 14, 1976

[54] OPTICAL THICKNESS DETECTING AND COMPARING METHOD AND APPARATUS

[75] Inventors: William F. Heckrodt, Menasha; Norman J. Van Hulle, Green Bay, both of Wis.

[73] Assignee: Presto Products, Incorporated, Appleton, Wis.

[22] Filed: Mar. 19, 1975

[21] Appl. No.: 559,995

[52] U.S. Cl. .......................... 250/560; 250/223 B; 356/239
[51] Int. Cl.² ........................................ G01N 21/30
[58] Field of Search ........ 250/222 R, 223 R, 223 B, 250/560, 358; 209/111.7; 356/108, 120, 239, 240

[56] References Cited
UNITED STATES PATENTS

| | | | |
|---|---|---|---|
| 3,427,110 | 2/1969 | Mansour | 356/239 |
| 3,439,178 | 4/1969 | Rottman | 250/222 R |
| 3,565,536 | 2/1971 | Wuellner et al. | 356/239 |
| 3,687,559 | 8/1972 | Fischer | 250/223 B |
| 3,716,136 | 2/1973 | Birner et al. | 209/111.7 |
| 3,880,750 | 4/1975 | Butler et al. | 250/223 B |
| 3,886,356 | 5/1975 | Gomm et al. | 356/240 |

*Primary Examiner*—David C. Nelms
*Attorney, Agent, or Firm*—Joseph P. House, Jr.

[57] ABSTRACT

Method and apparatus for detecting differences in the wall thickness of a hollow object at various locations around its perimeter. Radiant electromagnetic waves are directed through one side of the object. The intensity of the waves is sensed at two adjacent locations where they emerge from the other side of the object after the waves have passed through two wall portions of the object at different sides thereof. The intensity of said waves at said locations is compared to ascertain any difference in wall thickness at said locations. This comparison is repeated as the waves scan the perimeter of the object and the successive comparisons indicate any trend of wall thickness departure from an average thickness. Corrective measures can then be taken at the apparatus which fabricates the object to restore wall thickness to the desired amount. The invention has particular utility in monitoring and controlling wall thickness of extruded plastic tubing in the course of fabricating plastic bags.

24 Claims, 11 Drawing Figures

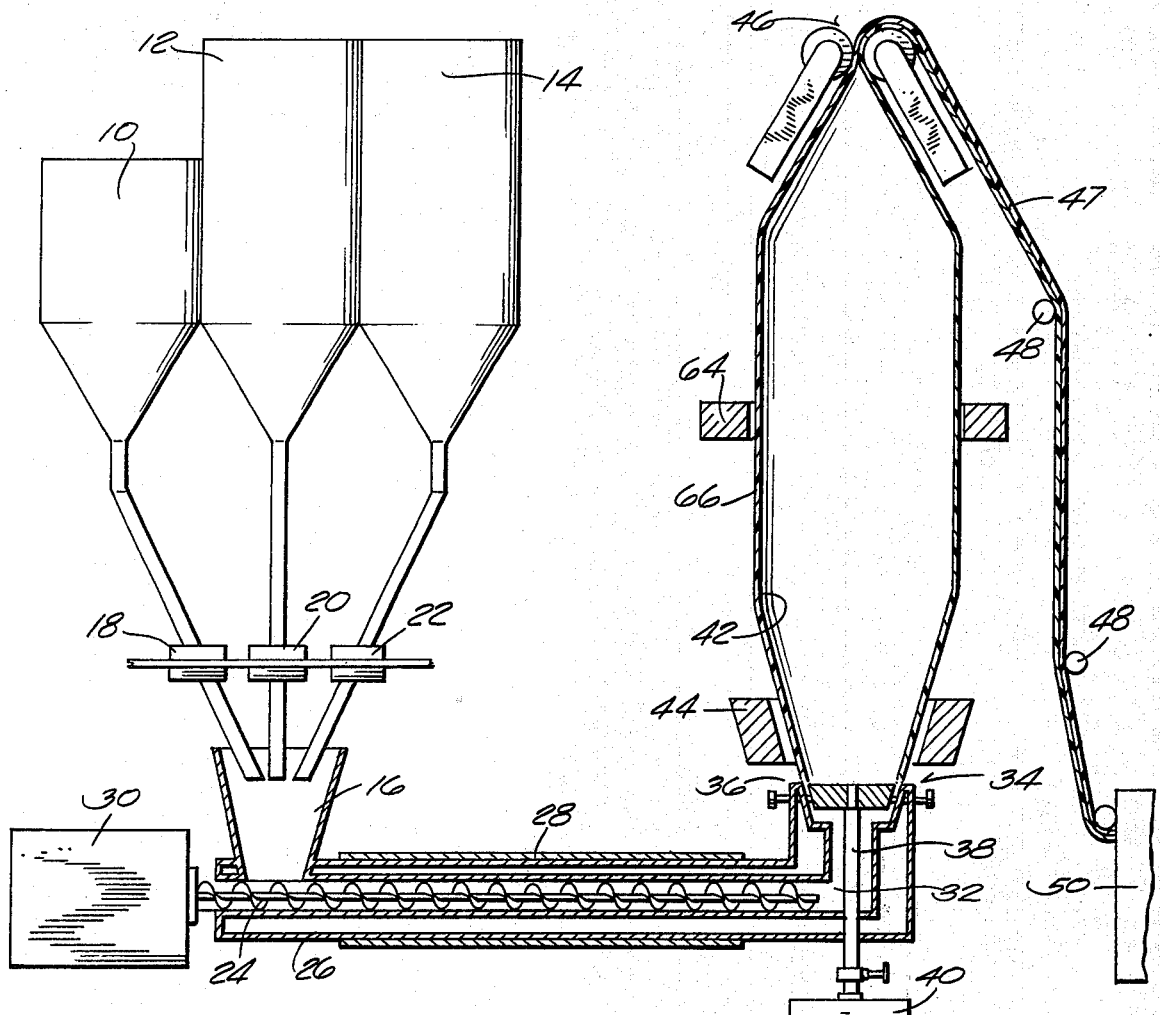

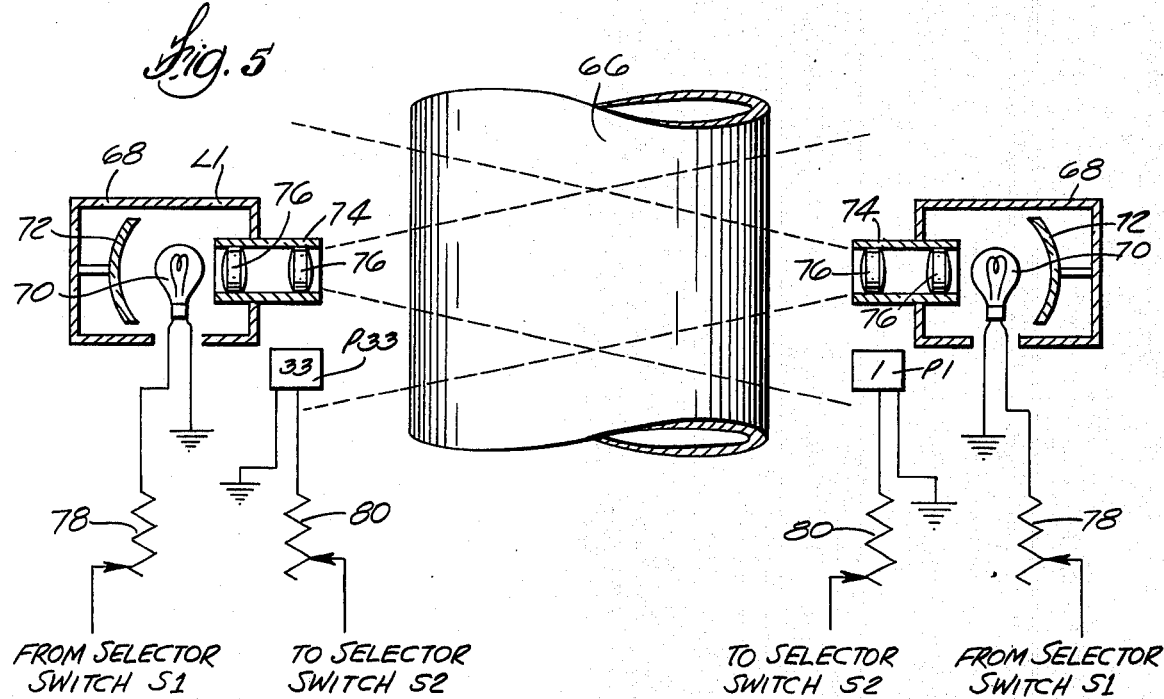
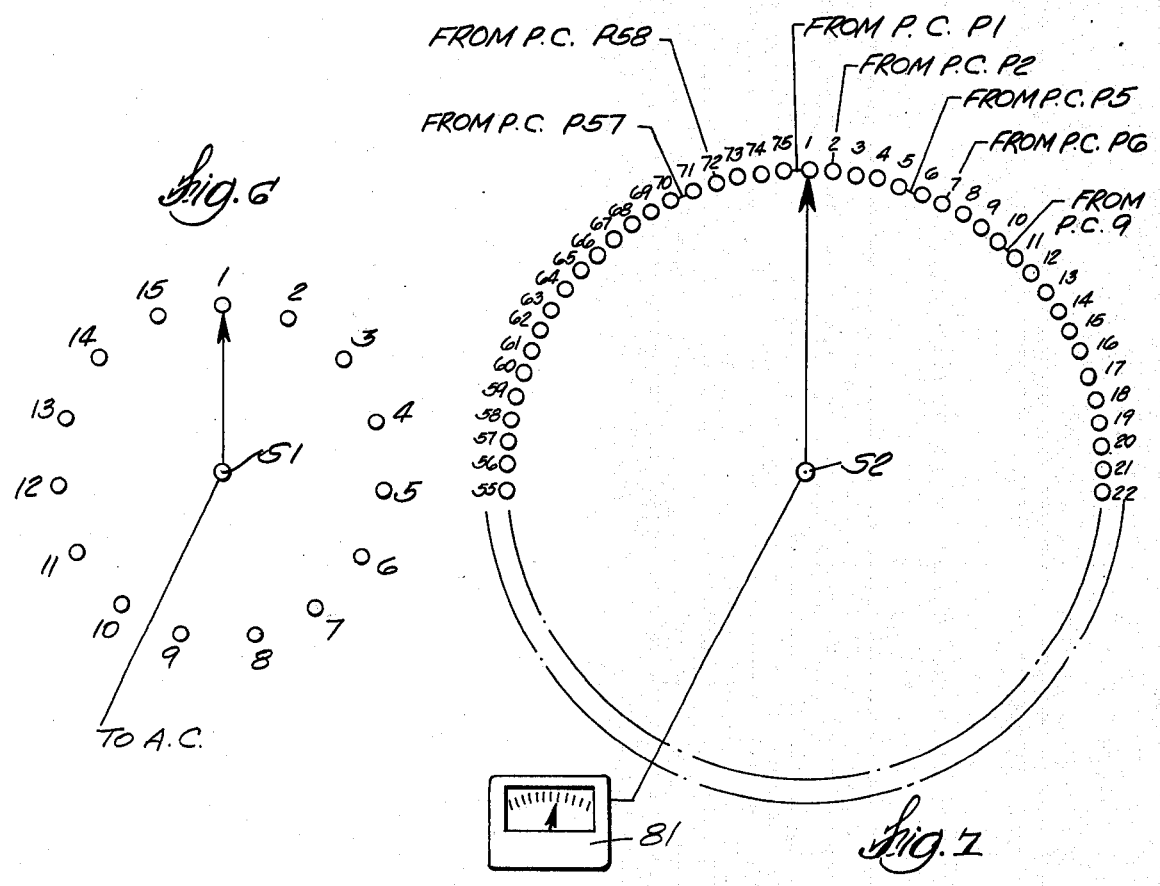

| SCAN | 1 | 2 | 3 | 4 | 5 | 6 | 7 | 8 | 9 | 10 | ----- | 24 | ----- | 60 | COUNT |
|---|---|---|---|---|---|---|---|---|---|---|---|---|---|---|---|
| 1 | 0 | +2 | +1 | -1 | +3 | +1 | -2 | -3 | +1 | -1 | | +3 | | -1 | 60 |
| 2 | 0 | +4 | +2 | -2 | +6 | +2 | -3 | -6 | +2 | -2 | | +6 | | -2 | 120 |
| 3 | +1 | +5 | +3 | -3 | +9 | +3 | -5 | -9 | +3 | -3 | | +9 | | -4 | 180 |
| 4 | 0 | +7 | +5 | -4 | +11 | +4 | -7 | -12 | +4 | -4 | | +12 | | -4 | 240 |
| | | | | | | | | | | | | | | | |
| | | | | | | | | | | | | | | | |
| SUM N | | | | | | | | | | | | | | | 60N/60 |
| AVERAGE | 0 | +2 | +1 | -1 | +3 | +1 | -2 | -3 | +1 | -1 | ----- | +3 | | -1 | N |

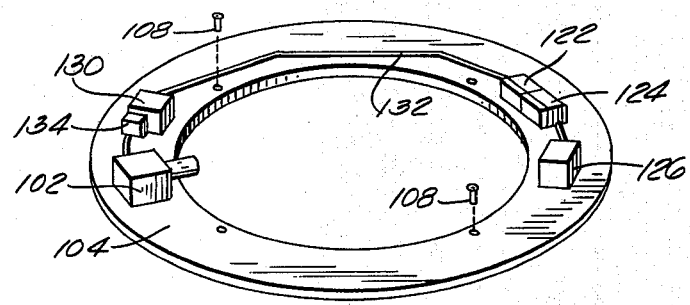
Fig. 11
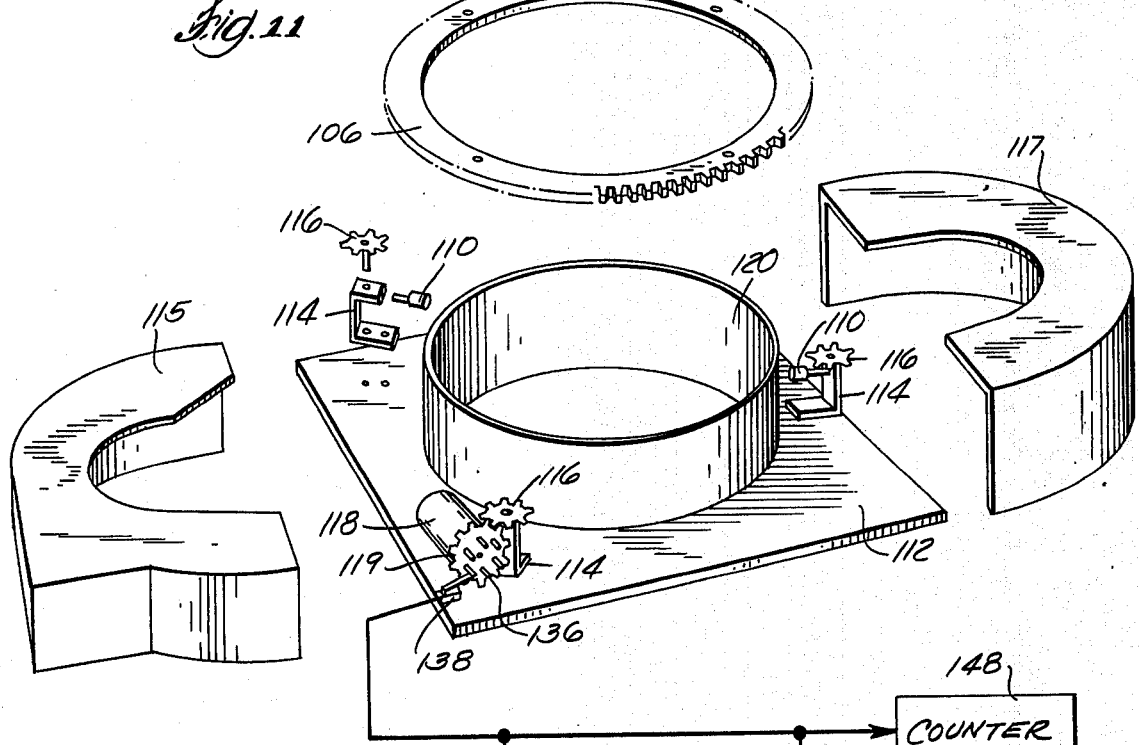
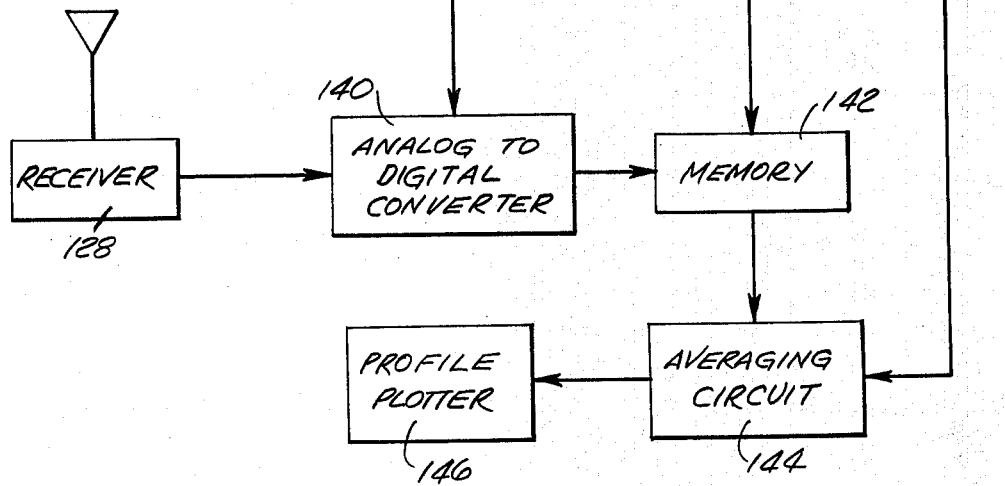

_3,980,890_

OPTICAL THICKNESS DETECTING AND COMPARING METHOD AND APPARATUS

BACKGROUND OF THE INVENTION

This invention relates to method and apparatus for detecting differences or non-uniformity in wall thickness around the perimeter of hollow translucent objects such as glass or plastic bottles or plastic tubing or the like.

In the past, apparatus has been proposed for measuring the wall thickness of glass or plastic bottles by shining one or more light beams through the bottle, sensing the intensity of the light beam with a photocell as it emerges from the bottle, and comparing the output of the photocell to a predetermined reference level which signifies a desired wall thickness for the bottle. Such apparatus is disclosed in U.S. Pat. No. 3,439,178 to H. R. Rottmann. However, such prior art apparatus has several drawbacks. In the first place, to measure the entire periphery of the bottle it is necessary to rotate the bottle through 360° while the light beam is shining through the bottle. This requires that the bottle be held in one axial position opposite the light beam while the bottle is rotated. This substantially slows down the rate at which the bottle can be processed. Also, the requirement that the bottles be rotated makes such prior art apparatus inapplicable to hollow objects which cannot be rotated, for example, plastic tubing which is being continuously extruded from a ring-shaped extrusion die. Moreover, such prior art apparatus is based on the theory that the opacity of the hollow object under measurement is directly proportional to its wall thickness. This may be true in some applications, but in the case of plastic tubing which is continuously extruded from a die, it has been found that the opacity of the tubing varies from batch to batch of plastic without regard to the wall thickness of the tube. The assumption that opacity is proportional to wall thickness only holds for adjacent regions of tubing which are close enough together to have been formed from substantially similar raw materials under substantially similar conditions.

Because of the aforementioned problems, most commercial plastic tube forming operations make no attempt to scan the tubing as it is formed, but simply measure the wall thickness of completed portions of the tube with a caliper or the like and make adjustments in the extruding die in accordance with such measurements. This is a time-consuming process and large quantities of tubing are formed before the measurement is taken. Accordingly, where unacceptable variations in wall thickness are discovered, this technique results in considerable waste.

SUMMARY OF THE INVENTION

In accordance with this invention, the tubing is continuously scanned as it issues from the extruding die and information is obtained which is utilized at an early stage to make adjustments in die settings, before large quantities of unacceptable tubing are formed. In accordance with this invention, radiant electromagnetic waves are directed through a hollow object which is semi-opaque to the wave frequency employed. The intensity of the waves is sensed at different locations around the hollow object, as the waves emerge from the far side of the hollow object. The intensity of the waves at said locations are compared to ascertain any difference in wall thickness at such locations. In some embodiments, the intensity measurement differences are recorded and stored in a computer memory. The differences may be plotted to provide a visual representation of the relative wall thickness along the path traced by the radiant energy waves around the hollow object.

In the case of continuously extruded plastic tubing, wall thickness non-uniformities as thus detected are utilized to adjust the extruder die and reduce or eliminate the non-uniformities and produce tubing having more uniform thickness.

In some embodiments the waves are generated by a wave source which is physically rotated about the perimeter of the object. In another embodiment the waves are generated by a series of stationary wave sources disposed in a ring around the perimeter of the object. The wave sources are sequentially energized to simulate a beam sweeping around the object.

Other objects, features and advantages of the invention will appear from the disclosure hereof.

DESCRIPTION OF THE DRAWINGS

FIG. 1 is a diagrammatic side elevation view of conventional apparatus for continuously extruding a thin-walled plastic tube through a ring-shaped extrusion die.

FIG. 2 is a fragmentary perspective view of the ring-shaped extrusion die shown in FIG. 1.

FIG. 3 is a fragmentary cross-sectional view taken on the line 3—3 of FIG. 2.

FIG. 5 is a diagrammatic cross-sectional view taken through the apparatus of FIG. 1.

FIG. 6 is a schematic diagram of a switch for sequentially energizing the projectors shown in FIGS. 4 and 5.

FIG. 7 is a schematic diagram of a switch for sequentially energizing the photocells shown in FIGS. 4 and 5.

FIG. 11 is an exploded perspective view of another embodiment of the invention utilizing a single light projector which is physically rotated around the tubing and having a pair of photocells which are connected in series opposition to each other to provide a difference output signal therefrom.

DESCRIPTION OF THE PREFERRED EMBODIMENTS

Figure 4:
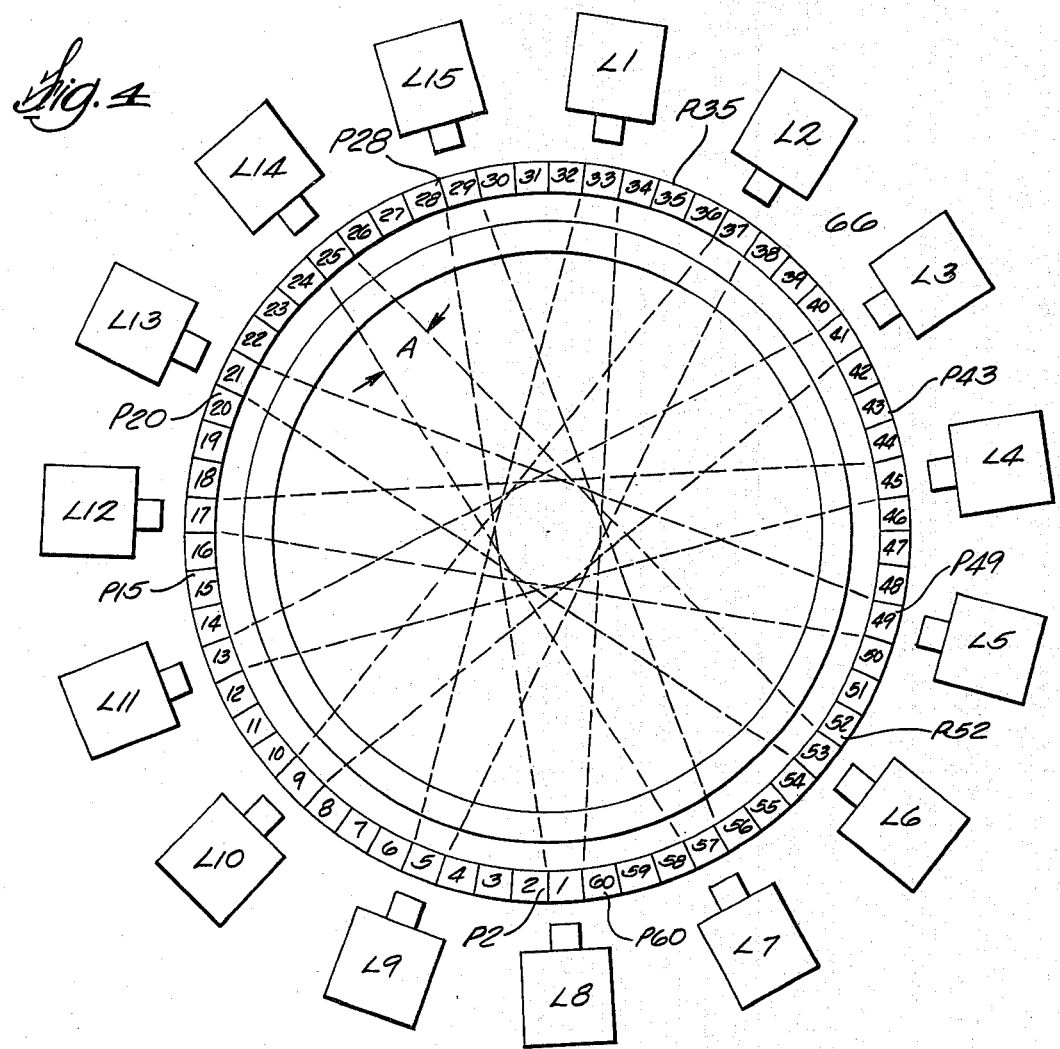
FIG. 4 is a plan view of the one embodiment of apparatus including a ring of light projectors and photocells around a plastic tubing.

Although the disclosurue hereof is detailed and exact to enable those skilled in the art to practice the invention, the physical embodiments herein disclosed merely exemplify the invention which may be embodied in other specific structure. The scope of the invention is defined in the claims appended hereto.

Although the method and apparatus of this invention is applicable to many different types of hollow objects, it was developed for use in connection with apparatus for continuously extruding a plastic tube from a ring-shaped die and will be described in connection with such apparatus.

FIGS. 1, 2 and 3 shown conventional apparatus for continuously extruding plastic film material from a ring-shaped die and for forming a plastic tube out of such material. Typical raw material includes reclaimed polyethylene granules, new polyethylene granules, and color concentrate. These are stored in bins 10, 12 and 14 and are fed by gravity into a mixing hopper 16 through flow control means 18, 20, and 22.

From hopper 16 the mixed plastic material and color concentrate are fed by a screw 24 through a feed tube 26 past a heater sleeve 28 which melts the plastic and brings the molten plastic to a predetermined temperature. Feed screw 24 is driven at a predetermined rate by a suitable drive motor 30. Feed screw 24 terminates in a cavity 32 below 32 a ring-shaped extrusion die 34 having a ring-shaped die slit 36 through which the molten plastic in both pressed from below and drawn from above to form tubing 66.

An air channel 38 extends through the center of die 34 and conducts compressed air from an air supply 40 to the center of the extruded molten plastic tube to case the tube to expand as it leaves the die slit 36 and to continue expanding until it reaches a frost line 42 at which the plastic material of the tube is solidified and thereafter maintains the same dimensions.

Solidification of the plastic is speeded up by a ring of cooling air jets 44 which blow cool air on the exterior of the extruded tubing 66 as it leaves extrusion slit 36. The molten plastic material is drawn out of die slit 36 by means of a pair of driven nip rolls 46 and also by means of pressure imposed on the molten plastic by the feed screw 24 from below. The nip rolls 46 fold the extruded plastic tube 66 into a double thickness web 47 which is then conveyed via rollers 48 to a bag machine 50 which cuts the web into pieces of predetermined length and seals one end of the lengths to form bags for any one of a number of uses.

FIGS. 2 and 3 show the details of the extrusion die 34. The die includes a central plug portion 52 having a precision ground cylindrical outer surface 54 which forms the inside ring of the ring-shaped slit 36 through which the plastic tube 66 is extruded. Central plug portion 52 has a central air channel 38 through which air is forced as described previously. The outer surface 55 of cylindrical slit 36 is formed by a die ring 56 which is secured to an annular base 58 by means of hold-down bolts 60 which pass through slightly enlarged openings in die ring 56 so as to allow adjustability for the die ring. The position of die ring 56 is adjustable by means of a plurality of adjustment bolts 62 which extend through die ring 56 and bear against an adjacent surface 63 of the base 58. The adjustment bolts 62 are adjusted in opposed pairs, with one bolt being loosened first, and then the other bolt of the pair being tightened to move the die 56 into the slack left by the loosened bolt. This can be done for every pair of opposing bolts around the periphery of die ring 56 to control the dimensions of die slit 36 and thus to control the dimensions of the extruded plastic tubing.

The problem to which this invention is addressed is the problem of detecting variations in the wall thickness of the tubing 66 extruded from die slit 36 so as to enable the operator to correctly adjust the adjustment bolts 62 to provide relatively constant and uniform wall thickness all the way around the tubing 66. The sensing of the tubing thickness is taken as the tubing moves axially past a suitable sensing instrument which is placed anywhere along the extruded tubing 66 between the frost line 42 (FIG. 1) and the nip rolls 46. In FIG. 1, a suitable position for the measuring apparatus is diagrammatically illustrated at 64.

A typical extruding apparatus as described above may have a screw 24 three inches in diameter, a die slit 36 which is ten inches in diameter with a slit opening of 0.030 inches in width. A typical tube 66 of extruded plastic is expanded or blown from ten inches to twenty inches in diameter and is stretched by the nip rolls 46 until the wall thickness of the tubing is reduced from 0.030 inches to only 0.0015 inches. There may be eight or more die adjusting bolts 62 to adjust the width of the die slit 36 to control the wall thickness of the tubing. The average wall thickness of the tubing may also be controlled by changing the screw speed or the nip roll speed, but such changes cause the thickness of the tubing to increase or decrease around its entire perimeter at the same time.

In a practical application, the extruder might run at a rate of 480 pounds of plastic materials per hour, which produces 180 feet of tubing each minute or about 3 feet of tubing per second. Each time the machine is shut down to clean or change die 34, the adjustment bolts 62 must be used to adjust the wall thickness of the extruded tubing. This is normally done once every week or two. In this particular example, under proper operating conditions, the optimum wall thickness of the extruded tubing is 0.0015 inches. A variation from 0.0013 inches through 0.0017 inches is acceptable. Such variations of wall thickness may be caused by misalignment of the extrusion die and also by short term variations in the screw speed or the nip roll speed. When the thickness of the tubing falls below 0.0013 inches, the tubing must be rejected. In the past, however, there has been no way to detect that the tube wall thickness had fallen below the lower tolerance level except by measuring the tube or bags formed therefrom after they were made. This required a good deal of time, and a great number of defective bags could be run between the time that the wall thickness fell below the lower tolerance level and the time that this condition was discovered by quality control measurements. Also, when it was determined that the bags were out of tolerance, there was no way to know which of the adjustment bolts 62 should be turned to bring the bag back into tolerance or how far they should be turned.

One solution to the problem is to make the bags thicker than necessary so that none of the thinnest spots fall below specification. However, if the extra thickness is just 0.0001 inches, this provides a total increase of weight of 7.5 percent in the bags. This represents a 7.5 percent material loss. Accordingly, to achieve the same end by adjustment of the extrusion die would result in a material saving of 7.5 percent.

In the method of this invention, waves of electromagnetic radiation such as light are directed or beamed through the wall of the tubing and the beam is scanned or rotated around the tubing perimeter. The intensity of the light waves emerging from the far side of the tubing is sensed or measured at predetermined sensing positions around the tubing. The light intensity measurements at adjacent measurement positions are then compared, such as by subtracting one measurement from the other. The differences are noted, and can be plotted on a chart to present a visual profile of the relative wall thickness along the path traversed by the light beam.

In the disclosed example, the tubing to be scanned is moved axially past the light source. The light source is moved on an effective circular path about the tube, whereby the light beam tranverses a helical path about the moving tubing. In other examples, however, the object to be scanned may be stationary. In such a case the light beam will transverse a circular path around the measured object. In the illustrated embodiment where the object being measured is moving axially through the light beam, it may be desirable to rotate the light beam several times around the object and then to average the measurements, thus to obtain an average relative thickness profile along the helical path.

As the light beam passes through the walls of the plastic tubing, the intensity of the beam is attenuated by an amount which is proportional to the opacity of the tubing. Although the opacity of tubing can vary due to factors other than the thickness of the tubing, it has been found that when small areas of the tubing are measured sufficiently close to each other, the opacity of the tubing is substantially proportional to the wall thickness of the scanned area, and therefor if the intensity of the light beam varies between adjacent scanned positions, this is an indication of a variation in the wall thickness of the tubing. The amount of variation of wall thickness is substantially proportional to the amount of variation in the measured intensity. Therefore, by plotting a graph of the difference measurement between adjacent measurement areas, an accurate profile of the tube wall thickness can be obtained which is valid in spite of variations in the opacity of the tubing due to variation in the coloring material or in the plastic material used.

The fact that measurements of adjacent areas are compared to each other to determine the variations of wall thickness is an important feature of this invention because it renders the measurement of wall thickness independent of variations of opacity. In the previously mentioned prior art method of U.S. Pat. No. 3,439,178, the measurement of light intensity is not compared to an adjacent intensity measurement, but is compared to a predetermined intensity standard. However, when light intensity measurements are compared to a predetermined standard, the intensity measurements are not a valid measure of wall thickness, since opacity can vary with the amount of coloring material put in the plastic.

Ordinary incandescent lamps can be used in the method of this invention to measure materials which are semiopaque to frequencies in the center of the visible frequency spectrum. However, there are some materials which are transparent to frequencies in the center of the visible spectrum but are semi-opaque to other frequencies. For example, clear polyethulene is semi-opaque to certain frequencies in the infra-red range. Clear glass is semi-opaque to certain frequencies in the ultra-violet range. Therefore, transparent materials such as clear polyethylene and clear glass can also be measured by the method of this invention through the use of appropriate radiant wave sources and/or filters. Other forms of electromagnetic radiation, such as beta or gamma rays, can be used for other applications of the invention. In general terms, any type of radiation can be used that will be attenuated by the material of the tubing so that the intensity of the radiation emerging from the far side of the tubing is proportional to the thickness of the tubing.

FIG. 4 shows one embodiment of the invention in which a plurality of light projectors L1 through L15 are arranged at position 64 of FIG. 1 in a ring around the extruded tube 66 which is moving axially with respect to the ring of light sources. A ring of photocells P1 through P60 are also arranged around the tubing 66 in such position as to intercept the light beams from opposing light projectors. As shown in FIG. 5 each light projector L1 through L15 comprises a casing 68, an incandescent lamp 70 within casing 68, a reflector 72 opposite one side of lamp 70, and a tube 74 which contains lenses 76 which produce a conically shaped light beam output. Each lamp 70 has a rheostat 78 connected in series therewith for varying the intensity of the light beam output from each particular projector. The photocells P1 through P60 are mounted as shown in FIGS. 4 and 5 so as to fall within the illumination cone of an opposite light projector. Each photocell P1 through P60 has a potentiometer 80 connected thereto for adjusting the output intensity of the photocell. The above noted components are all mounted on a suitable annular supporting framework which is not shown in the drawings but which will be obvious to those skilled in the art.

As shown in FIG. 4, the apex angle A of the illumination cones of adjacent projectors is selected to cause the cones to overlap at each fifth photocell. For example, the light cone from projector L1 illuminates photocells P1 through P5. The light cone from projector L2 illuminates the photocells P5 through P9, whereby the photocell P5 is illuminated both by projector L1 and by projector L2. Photocell P9 is illuminated both by projectors L2 and L3, and photocell P13 is illuminated both by projectors L3 and L4, and so on around the ring. The reason for this overlapped illumination of every fifth photocell is to provide a correction for differing intensities of illumination by the various lamps. In the operation of this embodiment, each of the projectors L1 through L15 is switched on and off in sequence to provide the equivalent of a single rotating beam. For sake of illustration, assume that the projector L1 is turned on first. This illuminates the photocells P1 through P5. While projector L1 is turned on the outputs of the photocells P1 through P5 are sensed or measured in sequence and the adjacent photocell readings are subtracted from each other. The reading of photocell P2 is subtracted from the reading of photocell P1, the reading of photocell P3 is subtracted from the reading of photocell P2, and so on. After the reading of photocell P5 has been subtracted from the reading of photocell P4, projector L1 is switched off and projector L2 is switched on, thereby illuminating photocells P5 through P9. It will be noted that photocell P5 receives illumination twice in this sequence, first from projector L1, and then from projector L2.

In the simplest form of this invention, the above-described switching can be executed by manually operated switches S1 and S2 as shown in FIGS. 6 and 7 which are connected respectively to the lamps 70 of projectors L1 through L15 and to the output of the photocells P1 through P60. The arm of switch S2 is connected to a meter 81. In this particular example, every fifth photocell P5, P9, P13 and so on, which are illuminated by two overlapping light beams, are coupled to two adjacent positions on the switch S2 so as to enable two successive measurements of those photocells. For example, photocell P5 is connected both to the fifth and sixth step on switch S2. This enables the two measurements on every fifth photocell to be conducted expeditiously.

Because of the excessive time involved in manually turning the switches, the manually operated embodiment is only useful in cases where the object to be measured is stationary or moving relatively slowly. In cases where the tubing 66 is moving at relatively high speed past the light sources and photocells, automatic measuring apparatus must be employed. Such apparatus is shown in the block diagram of FIG. 8.

Figure 8:
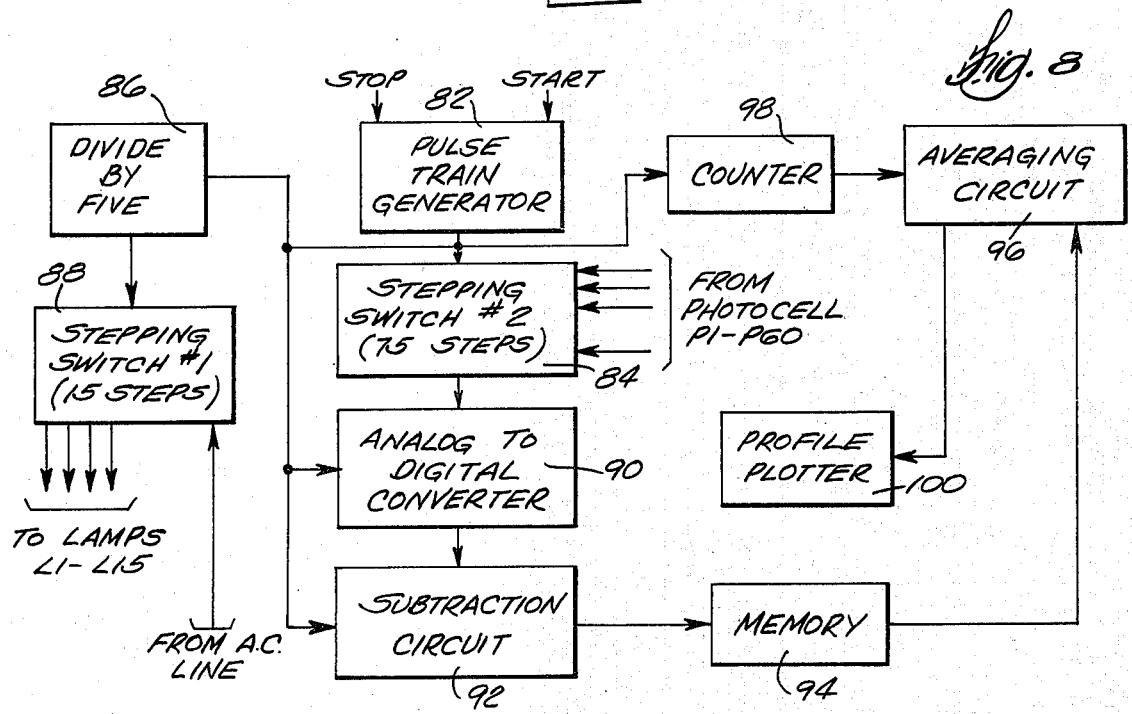
FIG. 8 is a block diagram of an electric circuit for automatically energizing the projectors shown in FIGS. 4 and 5 in sequence and for sequentially connecting the output of the photocells through a subtraction circuit, memory circuit, averaging circuit, and profile plotter to automatically plot a relative wall thichness profile of the tubing being measured.
Figures 9, 10:
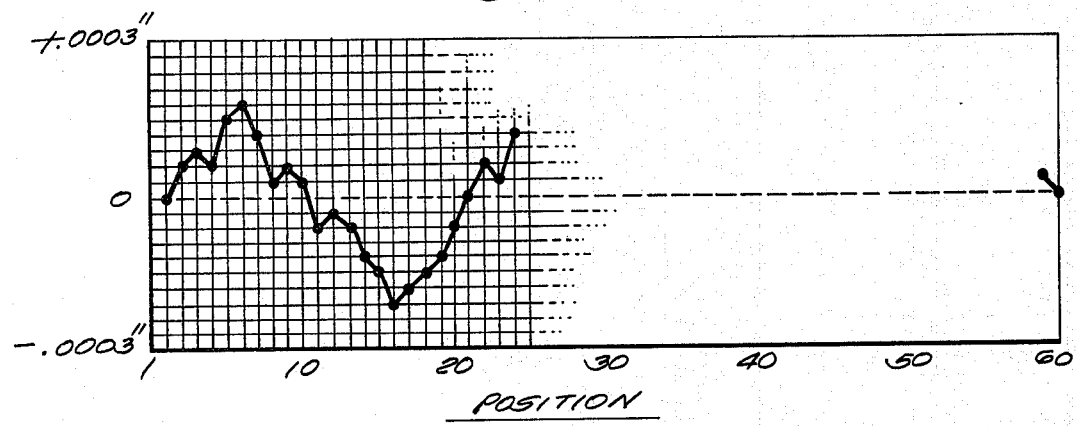
FIG. 9 is a graph showing a relative wall thickness profile plot taken by the apparatus of FIGS. 4 and 8.
FIG. 10 is a chart showing how the difference measurements are stored in a computer memory for a predetermined number of wave scans around the tubing and are subsequently averaged to provide an average relative wall thickness profile of the tubing.

Referring to FIG. 8, a pulse train generator 82 applies pulses to a 75 stepping switch 84 which is coupled to the photocells P1 through P60 according to the hookup shown in FIG. 7. The output of pulse train generator 82 is also applied to a divide-by-five circuit 86 whose output is applied to a 15 step stepping switch 88. Stepping switch 88 is coupled between the AC line and the input to the lamps 70 in projectors L1 through L15. Because of divide-by-five circuit 86, stepping switch 88 moves one step for every five steps of stepping switch 84. The output of stepping switch 84, which is the output of the photocells P1–P60 taken in sequence, is applied to an analog-to-digital converter 90 and from there to a subtraction circuit 92 which subtracts each adjacent pair of measurments as described previously. The results of subtraction circuit 92 are applied to a suitable computer memory 94 and are stored therein. After a predetermined number of measurements have been taken, the measurements stored in memory 94 are averaged in an averaging circuit 96 which is actuated by a counter 98. Counter 98 can be set to actuate averaging circuit 96 for any desired number of revolutions of the light beam around the tubing 66. The output of averaging circuit 96 is then applied to a profile plotter 100 whose output is a wall thickness profile plot such as shown in FIG. 9. The output of profile plotter 100 is the average of all the difference measurements taken at every measurement station.

FIG. 10 shows the manner in which the information is stored in the computer memory 94. The differences between adjacent measurements at each photocell position are identified and stored for each scan, which corresponds to the horizontal rows of information. After a predetermined number of complete scans, the different readings at each position are averaged as shown along the vertical columns. The position numbers are shown in the topmost horizontal row. The average values which are shown along the bottom horizontal row are then plotted as the thickness profile graph as shown in FIG. 9. The ordinate on the graph of FIG. 9 is calibrated in thickness. The 0 line indicates average thickness. The positive graduations indicate above average thickness. The negative graduations indicate below average thickness.

The objective of measuring or sensing differences in radiation beam intensity passing through adjacent areas of the tubing wall can also be accomplished by a single wave projector which is mounted on a ring platform and rotated around the tubing with one or more photocells mounted in the projectors's beam. Apparatus of this type is shown in FIG. 11.

Referring to FIG. 11, a projector 102, which can be similar to the projectors described previously, is mounted on an annular ring platform 104. A gear ring 106 is attached to platform ring 104 by bolts 108 and both rings are supported by rollers 110 which are mounted on top of a supporting base 112 by brackets 114. Brackets 114 also support gears 116 which engage gear ring 106 and hold it in position. One of the gears 116 is driven by a motor 118 through gear 119 to rotate the rings 104 and 106 continuously around a central collar 120. Rings 104 and 106 are normally covered by a housing consisting of two half shells 115 and 117.

Two photocells 122 and 124 are mounted on platform 104 opposite the light projector 102 and are connected together in series opposition so that the combined output of the two photocells is equal to the difference between their two output signals. This difference output signal is applied to a small FM radio transmitter 126 which continuously broadcasts the data to an FM radio receiver 128. Power for FM transmitter 126 is derived from a battery 130 via cables 132. Battery 130 also provides the power for projector 102 via a chopper 134 which modulates the light beam to avoid inteference caused by fluorescent lighting or other ambient radiation.

A circular array of pegs 136 is mounted on the gear 119 of motor 118 and serves to periodically trip a switch 138 whose output serves as a gate to trigger the output of FM receiver 128 into an analog-to-digital converter 140 whose output is applied to a memory circuit 142. Each entry in memory circuit 142 is an intensity difference signal measured at a predetermined position around the tubing under measurement. After a predetermined number of complete revolutions of rings 104 and 106, which is determined by counter 148, the difference readings stored in memory circuit 142 are averaged for each position by an averaging circuit 144, and the average values are applied to a profile plotter 146 which plots an average wall thickness profile such as shown in FIG. 9. This thickness profile can be used in adjusting the tubing extrusion die as described previously.

The averaging of the measurements and plotting of the profiles can also be carried out manually with the apparatus of FIGS. 4–7 on the forms shown in FIGS. 9 and 10. To do this, the output of photocells P1–P60 (FIG. 4) are read out in sequence as described previously and are recorded in any convenient manner. The difference between the output of adjacent photocells P1–P60 is computed and recorded on the form in FIG. 10. Each vertical column of the form in FIG. 10 contains the difference between the output of a corresponding pair of photocells. For example, column No. 1 contains the difference between photocell P1 and P2; column No. 2 contains the difference between photocell P2 and P3; and so on to column 60 which contains the difference between photocell P60 and P1. Each numbered horizontal row of the form in FIG. 10 contains the difference readings for one complete scan of photocells P1–P60. In the row labeled "sum", the sum of all values in each column is entered. In the row labeled "average", the average of the values for each column is entered. The values in the average row are plotted to give the profile shown in FIG. 9.

What is claimed is:
1. A method of detecting differences in the wall thickness of a hollow object comprising the steps of directing radiant electromagnetic waves through one side of said object, sensing the intensity of said electromagnetic waves where they emerge from another side of the object, said method being characterized by sens- ing the intensity of said waves at two adjacent measurement areas at said other side of the object and comparing the intensity of said waves at said measurement areas to ascertain any difference in wall thickness between said measurement areas.

2. The method of claim 2 in which said hollow object comprises an axially moving tube, said two adjacent measurement areas being circumferentially spaced about said tube.

3. The method of claim 1 in which the intensity of said waves is sensed at additional different measurement areas around the circumference of said object, and wherein the intensity of said waves is compared at different pairs of adjacent measurement areas in time sequence to ascertain the relative wall thickness of said object at said adjacent measurement areas.

4. The method of claim 3 wherein said additional measurement areas extend completely around said object and wherein the difference of wave intensity at adjacent measurement areas is plotted to provide a visual representation of the wall thickness profile of the object along the path traversed by said waves.

5. The method of claim 2 wherein the axially moving tube is continuously extruded through an adjustable extruder die, and further comprising the step of adjusting said die to correct wall thickness abnormalities detected by said comparison.

6. The method of claim 2 wherein several measurements are made at the same position relative to said object, and wherein the measurements at the same position are compared with measurements made at an adjacent position and the resulting quantity is averaged and the average values at adjacent successive positions are ascertained.

7. The method of claim 1 wherein said waves are generated by a wave source which is physically rotated around said object, the intensity of said waves being sensed by adjacent wave sensors which are physically rotated around said object opposite said wave source.

8. The method of claim 1 wherein said waves are generated by a series of wave sources positioned in a ring around said object, and further comprising the steps of sequentially energizing said wave sources, and sequentially sensing the intensity of said waves by a series of wave sensors positioned in a ring around said object.

9. The method of claim 8 wherein the waves beamed from adjacent wave sources overlap at their side edges, one of said wave sensors being located within the overlapped portion of each pair of overlapped beams so as to be responsive to waves from two wave sources, and further comprising the step of calibrating intensity measurements by comparing the output from said one sensor when responding to beams emanating from each of said two wave sources.

10. The method of claim 1 wherein said object is semi-opaque to the frequency of said electromagnetic waves.

11. Apparatus for detecting differences in the wall thickness of a hollow object at various measurement areas around its perimeter and comprising wave source means for directing radiant electromagnetic waves through one side of the object, wave sensor means for sensing the intensity of the waves at at least two adjacent measurement areas where the waves emerge from another side of the object, and means for comparing the intensity of said waves at said measurement areas to ascertain any differences in wall thickness between said measurement areas.

12. The apparatus of claim 11 wherein said hollow object is a length of extruded tubing and further comprising means for moving said tubing axially past said wave source means.

13. The apparatus of claim 11 further comprising means for directing said radiant electromagnetic waves in a beam and effectively rotating said beam around said object to scan its perimeter.

14. The apparatus of claim 13 in which the last mentioned means comprises a single wave source which is physically rotated about said object.

15. The apparatus of claim 13 in which the last mentioned means comprises a series of stationary wave sources located in a ring about said object, and means for sequentially energizing and de-energizing said wave sources to scan a beam around the object's perimeter.

16. The apparatus of claim 11 in further combination with means for plotting the difference of wave intensity at adjacent measurement areas around said object to provide a visual representation of the wall thickness profile of the object along the path traversed by said waves around said object.

17. The apparatus of claim 16 wherein said hollow object comprises an axially moving tube, and wherein several difference measurements are made at the same measurement position relative to said tube, and further comprising means for plotting values at adjacent measurement positions to provide a visual representation of the wall thickness profile of the tube along the path traversed by said waves around said tube.

18. The apparatus of claim 13 wherein said wave source means comprises a plurality of individual wave projectors disposed in a ring around said object, and means for energizing each wave projector in sequence, and wherein said wave sensor means comprises a plurality of wave sensors positioned in a ring around said tube, and means for selectively measuring the output of each sensor in time sequence.

19. The apparatus of claim 18 wherein the wave beams from adjacent wave projectors overlap at their side edges, one of said wave sensors being positioned within the overlapped portion of each pair of overlapped beams so as to be responsive to waves from both wave projectors, whereby a difference in wave source intensity can be determined.

20. The apparatus of claim 18 and further comprising a subtraction circuit coupled to the output of said sensor measuring means for subtracting the measurements of adjacent sensors in time sequence, a memory circuit coupled to the output of said subtraction circuit, and a profile plotter for plotting a visual representation of the sensor difference measurements around said hollow object.

21. The apparatus of claim 11 wherein said wave source is supported on a ring-shaped support surrounding said object, said support being mounted for rotation around said object, and wherein two wave sensors are mounted at adjacent locations on said support opposite said wave source, said two wave sensors being connected in series opposition so as to produce an output signal which is proportional to the difference of wave intensity at said adjacent measurement areas.

22. The apparatus of claim 21 and further comprising a radio transmitter on said support, means coupling the output of said sensors to said transmitter to be transmitted thereby, a radio receiver for receiving the signals transmitted by said transmitter, and means coupled to said radio receiver for plotting a visual representation of the difference measurements around said object.

23. The apparatus of claim 22 wherein said object comprises an axially moving length of tubing, and wherein said means coupled to said radio receiver comprises an analog-to-digital converter coupled to the output of said receiver, a memory circuit coupled to the output of said analog-to-digital converter, and a profile plotter for plotting a visual representation of the sensor difference measurements around said hollow object.

24. The apparatus of claim 11 in combination with a rotor for physically rotating said wave source means and said wave sensor means around the perimeter of said object.

* * * * *